United States Patent

Wajid et al.

Patent Number: 5,528,924
Date of Patent: Jun. 25, 1996

[54] ACOUSTIC TOOL FOR ANALYSIS OF A GASEOUS SUBSTANCE

[75] Inventors: Abdul Wajid, East Syracuse; Carl A. Gogol, Manlius, both of N.Y.

[73] Assignee: Leybold Inficon Inc., E. Syracuse, N.Y.

[21] Appl. No.: 158,562

[22] Filed: Nov. 29, 1993

[51] Int. Cl.⁶ .................................................. G01N 29/22
[52] U.S. Cl. ........................ 73/24.06; 73/31.05; 73/579
[58] Field of Search ................................. 73/23.2, 24.01, 73/24.06, 24.04, 24.05, 31.05, 579, 597

[56] References Cited

U.S. PATENT DOCUMENTS

| | | | |
|---|---|---|---|
| 2,653,471 | 9/1953 | Clewell | 73/24.01 |
| 2,775,885 | 1/1957 | Rassweiler et al. | 73/24.01 |
| 3,434,334 | 3/1969 | Vanderbussche | 73/24.01 |
| 3,468,157 | 9/1969 | Burke | 73/24.01 |
| 3,544,276 | 12/1970 | Merwitz, Sr. | 73/28.01 |
| 3,762,197 | 10/1973 | Roof et al. | 73/24.01 |
| 4,255,964 | 3/1981 | Morison | 73/24.01 |
| 4,280,183 | 7/1981 | Santi | 73/24.01 |
| 4,380,167 | 4/1983 | Longini | 73/24.01 |
| 4,616,501 | 10/1986 | Mechlenburg | 73/24.01 |
| 4,679,947 | 7/1987 | Miller et al. | 73/24.04 |
| 4,939,905 | 7/1990 | Manz | 62/77 |
| 5,060,506 | 10/1991 | Douglas | 73/24.01 |
| 5,060,507 | 10/1991 | Urmson et al. | 73/24.01 |
| 5,076,094 | 12/1991 | Frye et al. | 73/19.03 |
| 5,158,747 | 10/1992 | Manz et al. | 73/24.04 |
| 5,159,843 | 11/1992 | Shakkottai et al. | 73/24.05 |

Primary Examiner—Hezron E. Williams
Assistant Examiner—Rose M. Finley
Attorney, Agent, or Firm—Harris Beach & Wilcox

[57] ABSTRACT

An acoustic technique is employed to identify the species of a sample of refrigerant gas and whether it contains significant contaminants. The refrigerant is admitted into a Helmholtz resonator under controlled pressure, and a drive frequency is swept across a frequency band and applied to a first transducer. A second transducer picks up the vibrations in the resonator and the output signal is compared to the drive signal. The resonant peak or center frequencies are identified and the sharpness or quality factors are measured. These measured data are compared with stored data to identify the refrigerant.

22 Claims, 4 Drawing Sheets

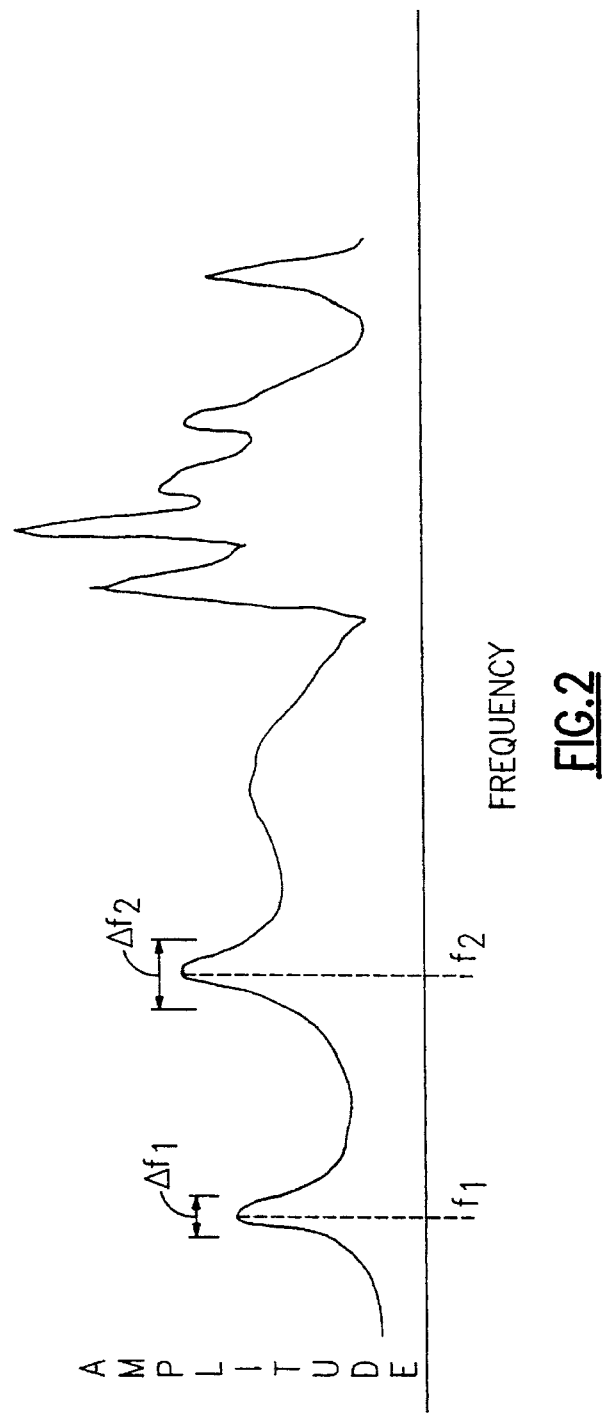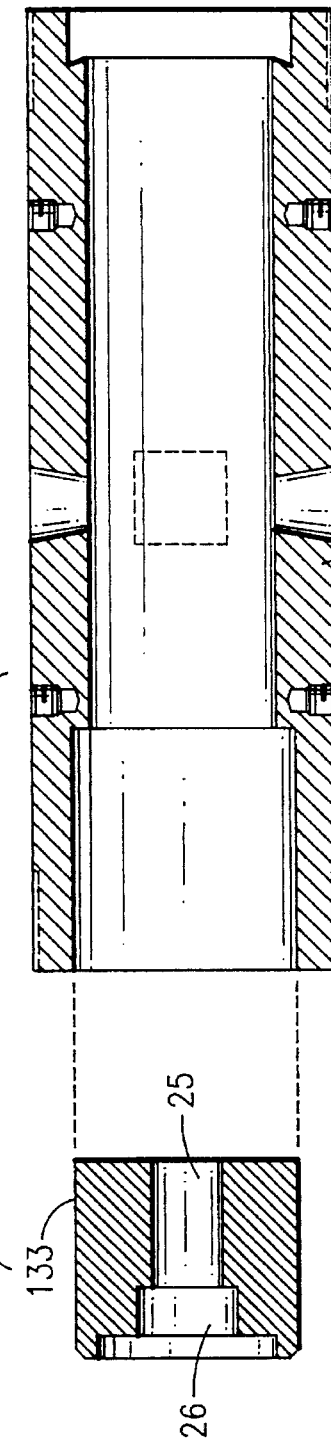

ACOUSTIC TOOL FOR ANALYSIS OF A GASEOUS SUBSTANCE

BACKGROUND OF THE INVENTION

The invent relates to a method and apparatus for identifying a gaseous substance and determining its purity, using acoustic techniques. The invention is more particularly concerned with identification of a gaseous substances of unknown species by analysis of frequency response of a resonator containing the substance in vapor form.

In the field of air conditioning service and repair, there is a need to identify the refrigerant charge contained in a system so that the refrigerant can be properly handled for reclamation and recycling, or for disposal. In recent years, because of environmental concerns, it has become the practice for air conditioner repair shops to capture and retain the used refrigerant in a reclamation system, rather than permit it to escape into the atmosphere. Also, because of the high cost of disposal of unreusable refrigerant, and because of the high cost of fresh refrigerant, economic needs have also driven air conditioner repair shops to reclaim the refrigerant charge in a reclaimer device provided for that purpose.

For similar environmental concerns, manufacturers of automotive air conditioning systems have begun to switch over from type R12 refrigerant (dichloro-difluoro methane) to another refrigerant, R134A, (1,1,1,2-tetrafluoroethane) which is believed to be gentler to the environment than R12 if it escapes to the atmosphere. Type R134A refrigerant was engineered to have thermal characteristics very similar to R12 refrigerant so that R134A based systems could be used where R12 systems are now used, i.e., in automotive air conditioning systems. On the other hand, R134A refrigerant is chemically incompatible with R12 refrigerant, and cannot be reused if one refrigerant is contaminated with the other. Also, if either refrigerant R12 or R134A has been contaminated with another refrigerant such as R22, the refrigerant should not be reused. However, if the refrigerant contains air or lubricant, the refrigerant can be deemed acceptable, because the reclaiming device can remove these impurities from the refrigerant.

Techniques of identifying a species of a fluid by means of its dielectric properties have been described e.g. in U.S. Pat. Nos. 5,150,683; 5,091,704; and 5,119,671. For example, the relative percentages of a gasoline/alcohol fuel mixture are measured by applying an RF signal to a coil submerged in the mixture. This system would not be workable for identifying which of two refrigerant species is present and if unacceptable contaminants are present in the refrigerant.

A technique to identify and distinguish between two different refrigerant gases, based on the dielectric properties of the gases, it described in U.S. Pat. No. 5,158,747. The device of that patent can also be configured to be responsive to acoustic properties of the refrigerant vapor, by sensing changes in velocity or phrase angle of acoustic waves traveling in the refrigerant vapor. However, this type of device is not precise enough to sense whether impurities are present in unacceptable levels.

OBJECTS AND SUMMARY OF THE INVENTION

It is an object of this invention to provide a technique for automatically determining the species of a refrigerant and the refrigerant's purity.

It is a more specific object of the invention to identify the species of an unknown gaseous substance, and to estimate its purity, by analysis of its acoustical properties.

It is another object to provide apparatus of simple design and reliable, rugged construction for accurately and repeatably carrying out this technique.

The refrigerant is tested by introducing a sample of it, in vapor form, into a resonant chamber, which in the preferred mode is a Helmholtz resonator, at a controlled vapor pressure, e.g., 2.25 psig. A Helmholtz resonator has the beneficial property of providing resonances at frequencies of a few hundred hertz in a unit of very compact size. The Helmholtz resonator can also be constructed so as to have plural resonances, if desired. In a preferred mode the resonant chamber is formed to produce two distinct resonances, and in the preferred construction the Helmholtz resonator has first and second necks, each of a respective length and area, connecting first and second volumes. A frequency generator produces a sweep of frequencies in a band that includes the two resonances, and this sweep is applied to a transducer in one of the first and second volumes. Another transducer, responsive to vibrations in the resonant chamber, produces an output signal that varies in response to the amplitude of the vibrations in the chamber. A digital circuit responsive to the frequency generator and second transducer output determines the center frequencies for the first and second resonances and also determines the frequency width of these resonances to determine quality or sharpness factors for the two resonances. Then these center frequencies and sharpness factors are compared with stored data concerning two or more candidate species of the refrigerant, and a determination is made as to the identity of the refrigerant species of the sample, and the extent and nature of any contaminants.

A thermal sensor in contact with the chamber is coupled to the digital circuit so that it can compensate for any temperature variations. The chamber is isolated from external environmental noise.

A regulator at the chamber inlet regulates vapor pressure at the sample gas to a predetermined level and in the preferred embodiment at 2.25 psig. The regulator also permits the chamber to be evacuated to twenty-nine inches of mercury below ambient.

In a preferred embodiment, the sweep of frequencies extends from about 300 Hz to 3 KHz.

The device can be calibrated using a known gas, for example air from the environment.

The above and many other objects, features and advantages of this invention will become apparent from the ensuing description of a preferred embodiment, to be read in conjunction with the accompanying Drawing.

BRIEF DESCRIPTION OF THE DRAWING

FIG. 2 is a typical acoustic frequency response chart of the device of this invention, showing first and second acoustic resonances.

FIG. 4 is a partial exploded view of an alternative two-part construction of the acoustic chamber.

DETAILED DESCRIPTION OF THE PREFERRED EMBODIMENT

Figure 1:
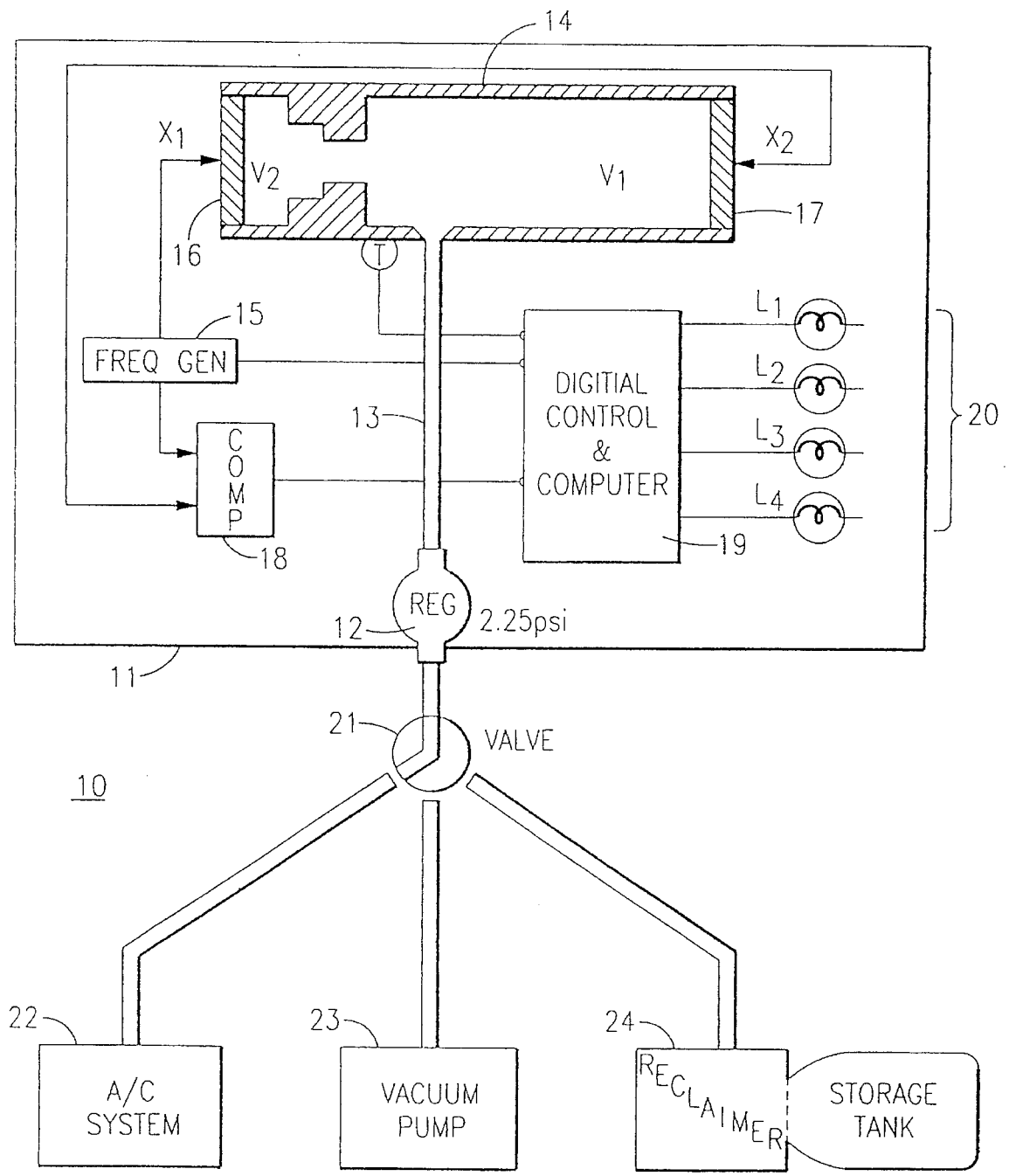
FIG. 1 is a system schematic of a refrigerant interrogation device according to an embodiment of the present invention.

With reference to the Drawing, and initially to FIG. 1, a refrigerant interrogation device 10 is configured to assess the species of a refrigerant gas and the refrigerant's purity. The principle of its operation is to utilize information that is derived by measuring the unknown gas's acoustic properties.

The measured data about the unknown sample gas physical parameters are then compared with stored, predetermined knowledge bases of the acoustical properties of two or more likely candidate refrigerants, and mixtures thereof. In addition to knowledge of the acoustic properties of various pure refrigerant gases, the technique of this invention also employs knowledge of the acoustic behavior of the target refrigerants in mixtures. The decision as to refrigerant species and purity can be made on the basis of any of several algorithms, and one successful technique utilizes logical values and best fit.

In the device 10 shown in FIG. 1, a housing 11 contains equipment beginning with an inlet regulator 12 that is coupled by a gas conduit 13 to a Helmholtz resonator 14, to be described briefly below. A frequency generator 15 generates a sweep of frequencies across a spectrum from about 300 Hz to about 3000 Hz, and applies the sweep of frequencies to an electroacoustic transducer 16 that is in contact with an interior volume $V_2$ of the resonator 14. A pickup transducer or microphone 17 in contact with another interior volume $V_1$ of the resonator senses vibrations in the volume $V_1$. This transducer 17 provides an output signal to a comparator 18. The comparator also receives the driving signal from the generator 15.

Each transducer 16,17 has an associated diaphragm in the form of a foil or membrane to isolate the microphone from the sample within the resonator. The diaphragms are tensioned and vacuum-tight. The foils or membranes protect the transducers from refrigerants that can be chemically active, and also protect the transducers from overpressure.

The frequency generator 15 provides a precision, frequency-variable drive signal for acoustically exciting the resonator 14. The generator is rapidly alterable in frequency to a precision of about 0.1 Hz. The comparator 18 then provides a sensitive and precise means of acoustic energy level detection, with sufficient resolution to identify resonant peaks to within about 0.1 Hz. The comparator 18 can operate, for example, on the basis of phase shifts as between the drive signal and pickup signal.

A digital control and computer 19 has an input coupled to the comparators 18 and a control output coupled to the generator 15. A temperature detector 20 in thermal communication with the resonator 14 provides a temperature signal to the digital control and computer 19. Based on the results of the test conducted with a given sample, the computer 19 will activate one of a group of indicator lamps or LEDs L1, L2, L3. These can be configured so that if the sample is identified as R12, lamp L1 is lit, or if the sample is identified as R134A, lamp L2 is lit. If the sample contains an unacceptable level of an adulterant, such as another refrigerant, the lamp L3 is lit. Another lamp or LED L4 can be provided to indicate that a test is in progress. An additional lamp can indicate, for example, that the cell has not been properly purged between uses, or that the sample contains air or another light gas such as propane.

Also shown in FIG. 1, the device 10 can be coupled via a selector valve 21 to each of an air conditioner, refrigerator, or heat-pump system 22, a vacuum pump 23, and a reclaimer device 24, each of which can be of any standard configuration. The regulator 12 permits the vacuum pump 23 to purge residual gases from the resonator 14 down to twenty-nine inches of mercury. The system 22 typically provides a refrigerant pressure of between about 35 to 400 psi, and the regulator 12 reduces this pressure to about 2.25 psi before admitting a sample of the refrigerant into the interior of the resonator.

The sample is tested, and if it is identified as a particular refrigerant without unacceptable levels of contaminants, the valve 21 can rotate so that the refrigerant charge from the air conditioner system 22 is supplied to the reclaimer device 24 for purging and storage. If the charge is identified as a refrigerant mixture or a refrigerant with an unacceptable contaminate level, the charge can be directed to a holding tank (not shown) for later disposal.

The resonator 14 shown in FIG. 1 is of the Helmholtz type, having first and second large volumes $V_1$, $V_2$, that are connected by first and second necks 25,26, here arranged in series. Each of the necks has a predetermined length $l_1$, $l_2$ and a predetermined cross sectional area $A_1$, $A_2$. First neck 25 is in fluid communication with first volume $V_1$ and second neck 26 and second neck 26 is in fluid communication with first neck 25 and second volume $V_2$.

Helmholtz resonators have natural frequencies $F_H$ that depend on the dimensions of the neck 25,26 and the speed of sound $C_o$ of the gas in the chamber. The general formula for the principal resonance frequency is $$(2\pi)^2 F_H^2 = C_o^2 \frac{A}{vl}$$

where $l$ and $A$ are the length and area of the neck, and $v$ is the effective volume, $v=1/(1/V_1+1/V_2)$ The resonator 14 with the two necks 25,26 will produce a pair of resonances $f_1$ and $f_2$. The volumes $V_1$, $V_2$ neck lengths $l_1$, $l_2$ and neck areas $A_1$, $A_2$ are fixed parameters, so the Helmholtz resonances $f_1$ and $f_2$ depend only on the speed of sound of the refrigerant gas.

FIG. 2 shows a typical resonance curve, in the frequency domain, for the Helmholtz resonator 14 containing an unknown sample refrigerant. The two necks 25,26 produce resonance peaks with respective peak or center frequencies $f_1$, $f_2$. Because of impurities in the sample, the resonances can vary in half-peak frequency width, here identified as $\Delta f_1$ and $\Delta f_2$. As is commonly understood these data provide a quality figure Q or resonance sharpness factor for each resonance, namely, $$Q_1 = \frac{f_1}{\Delta f_1} \qquad Q_2 = \frac{f_2}{\Delta f_2}$$

The resonances at the high-frequency end of the chart can be disregarded for these purposes.

In the technique of this invention, the frequency generator 15 drives the first transducer 16 with a sine wave of precise amplitude and frequency. An initial sweep is carried out at a fast rate to locate the approximate positions of the two resonances in the frequency domain. Then in the neighborhood of each of the resonances, the sweep of frequencies is carried out at a slower, more precise rate to identify the peak frequencies $f_1$ and $f_2$ and to measure the frequency half-widths $\Delta f_1$ and $\Delta f_2$. The frequencies and frequency half-widths are corrected to compensate for any temperature fluctuations.

Using the resonances frequencies $f_1$, $f_2$ and the sharpness or quality figures $Q_1$, $Q_2$, a value can be found for the equivalent inertial mass, m', of the refrigerant vapor.

For this, each of the two resonances can be considered as a driven harmonic oscillator, where displacement, x, of the gas within each of the necks 25,26 can be expressed in the equation.

$$m' \frac{d^2x}{dt^2} + Kx + 2\lambda \frac{dx}{dt} = A_o \cos 2\pi ft$$

where K is an equivalent spring constant, $\lambda$ is a damping factor, and $A_o$ is the amplitude of the driving frequency, which is considered a constant.

From elementary mechanics, it is understood that the natural resonance frequency F is $$F = \frac{1}{2\pi} \sqrt{\frac{K}{m'}}$$

while the damping factor $\lambda$ is related to the resonance sharpness Q according to the relationship $$\frac{\lambda}{m'} = \frac{2\pi F}{Q}$$

This leads to $$\frac{d^2x}{dt^2} + 4\pi^2 F^2 x + \frac{4\pi F}{Q} \frac{dx}{dt} = A_o \cos 2\pi Ft$$

In steady state, this yields $X(t) = X_o \cos(2\pi ft + \delta)$.

Here $\delta$ is a phase angle given by $$\tan \delta = -\frac{fF/Q}{F^2 - f^2}$$

The amplitude $X_o$ of the detected oscillations in the resonator is given by $$X_o(f) = \frac{A_o/m}{\sqrt{((2\pi F)^2 - (2\pi f)^2)^2 - (4\pi^2 Ff/Q)^2}}$$

Thus for each gas there is a set of resonance characteristics, namely a resonance frequency F, a quality factor (i.e. Q), and an effective mass m'.

This is also true for mixtures of the various refrigerants.

Within the digital control and computer 19 there are stored resonance behavior data for various refrigerants, e.g., R12, R22, and R134A, and mixtures of these in varying degrees of purity, i.e., R12/R22; R12/R134A; and R22/R134A. Data are also stored for mixtures of single species refrigerant with air and pump lubricants.

The two resonance center frequencies $f_1$, $f_2$ and two quality figures $Q_1$, $Q_2$ are used to determine the effective mass, m', and these are compared with stored data for each of the possible refrigerants R12, R134A, R22 in all of their possible ranges of mixtures. The resonant frequency data alone may provide somewhat ambiguous data, that is, pure R134A may have the same resonance frequency as a specific mixture of refrigerants R12 and R22. To resolve this ambiguity, the effective mass is computed and compared with the ranges of effective masses for pure R134A and R12/R22 mixtures. A match on one or the other of these will produce an unambiguous identification of the refrigerant as either pure R134A or impure R12 contaminated with R22.

The entire process of frequency sweeping, computing, comparing, and indicating the result takes only about thirty seconds.

Figure 3:
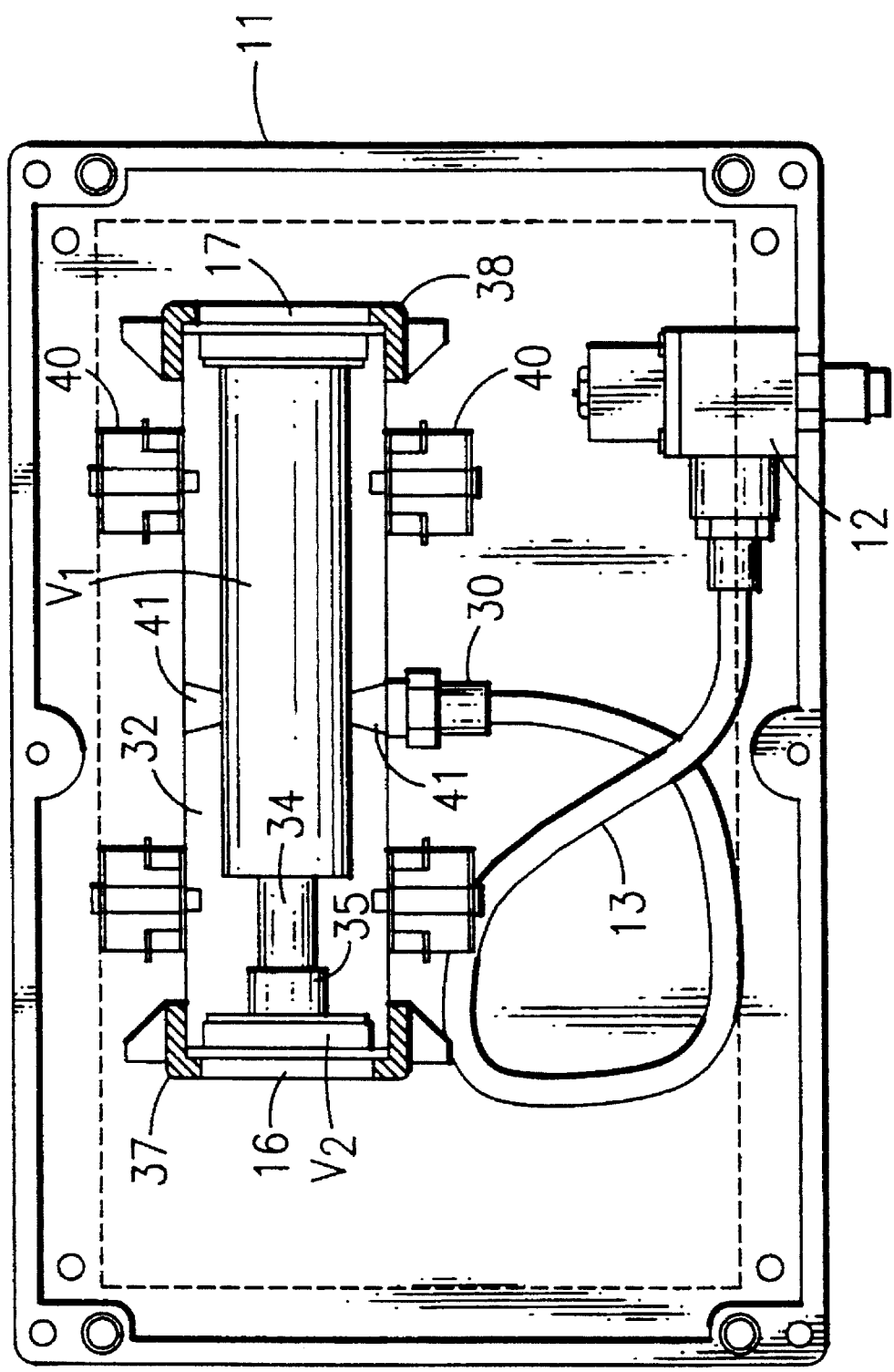
FIG. 3 is a plan view of one practical embodiment of the device of the present invention showing the acoustic chamber in cross section, and with a front cover removed from the housing thereof.

FIG. 3 illustrates a practical embodiment of this device 10, in which the housing 11 is here shown with a cover removed to expose its interior. Also, electronic elements and connections are omitted here but would be connected generally as shown in FIG. 1. The pressure regulator 12 has a nipple that penetrates the housing, and is connected by the line 13 to a fitting 30 that connects onto the resonator 14.

In this case, the resonator 14 is in the form of an aluminum cylinder 31 in which there are large axial bores 32 and 33 that create the respective volumes $V_1$ and $V_2$. A series of narrower bores 34 and 35 create the resonator necks 25 and 26. A pair of end caps 37 and 38 screw on to threads on the ends of the cylinder 31 to retain the microphones 16,17.

Vibration-damping mountings 39 and 40 are fitted to the base of the housing 11 and to the cylinder 31 to mount the same in the housing, and at the same time to isolate the resonator from environmental noise.

There are a pair of opposed receptacles 41,41 in the cylinder 31, with the fitting 30 being mounted into one and the thermal sensor (not shown here) being fitted into the other.

In a variation of this embodiment, a two-piece cylinder 13 is employed for the resonator, as shown in the exploded partial view of FIG. 4. Here the cylinder comprises an outer sleeve 132 and an inner cylindrical plug 133. The plug 133 contains the two necks or smaller bores. This arrangement can be somewhat simpler to machine and manufacture in large quantities. The plug 133 can be made of a different material from that of the outer sleeve 132, e.g., molded of a durable plastic resin.

Returning to FIG. 3, the regulator 12 should have the following characteristics. The regulator should accommodate a vacuum purge (29 inches Hg) of the resonator through the inlet nipple. The regulator valve must accommodate all conventional refrigerants and their lubricants over a range of pressure from 35 psig to 500 psig. On the controlled side, i.e., at the resonator 14, the regulator should have a reproducability of 0.25 psi, and produce a regulated pressure of 2.25 psig. Because the refrigerant can be taken from the system 22 at any of various points in its refrigeration cycle, the regulator is operable over a temperature range of –40° F. to 185° F., and up to 750 psig pressure.

The microphones 16,17 or other acoustic transducers should be selected to have their natural resonances well above the sweep frequency range, i.e., well above 3 KHz.

In alternative embodiments, the pressure within the resonator 14 can be measured rather than regulated, and the algorithm can compensate for the effect of pressure variations on the resonances.

In some possible embodiments, a Helmholtz resonator or other resonator can provide for a single resonance only, while in still other possible embodiments the resonator can provide for three or more resonances.

Figure 5:
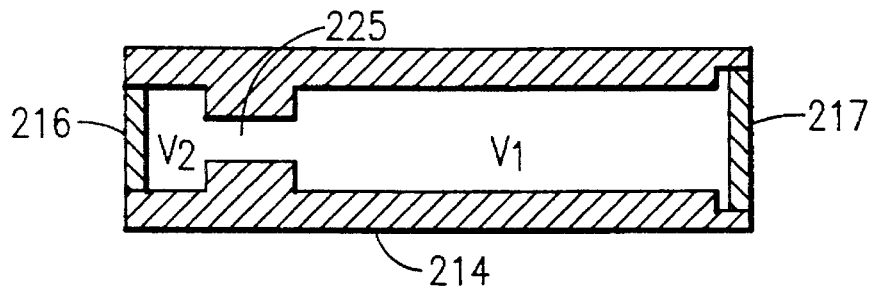
FIG. 5 is a schematic view of a resonator that can be employed in an alternative embodiment.

One simplified embodiment can be explained with respect to FIG. 5 which shows a single resonance Helmholtz resonator 214, with chambers forming volumes $V_2$, $V_1$ and a single neck 225 separating the two. A pair of microphone 216,217 or other transducers are disposed in contact with the gas in the resonator 214.

Figure 6:
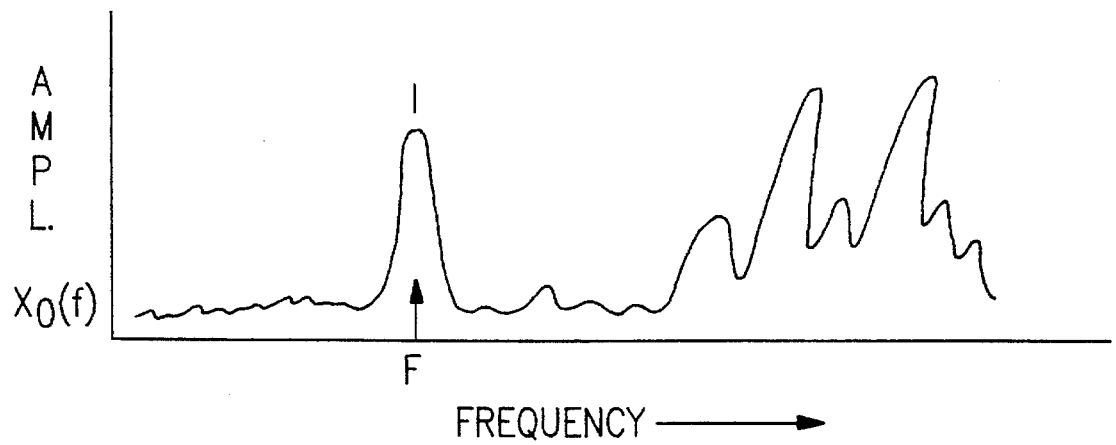
FIGS. 6 and 7 are frequency response charts for explaining this embodiment.

This configuration provides a single Helmholtz resonance F as shown on the chart of FIG. 6.

It should be noted that while the amplitude $X_o(f)$ at any given frequency of vibrations in the chamber is not directly observed, the oscillators create pressure deviations which create microphone output voltages y(f) on the second transducer 216. This output voltage is proportional to the amplitude.

$$y(f) = K * X_o(f)$$

where K is a microphone gain factor.

The gain factor K can be derived by taking a measurement at a frequency far below the resonance F. In this example, a frequency f=333 Hz is used. This step makes the operation of the device independent of microphone characteristics, which can vary from one device to another and can also vary as the microphone ages.

Figure 7:
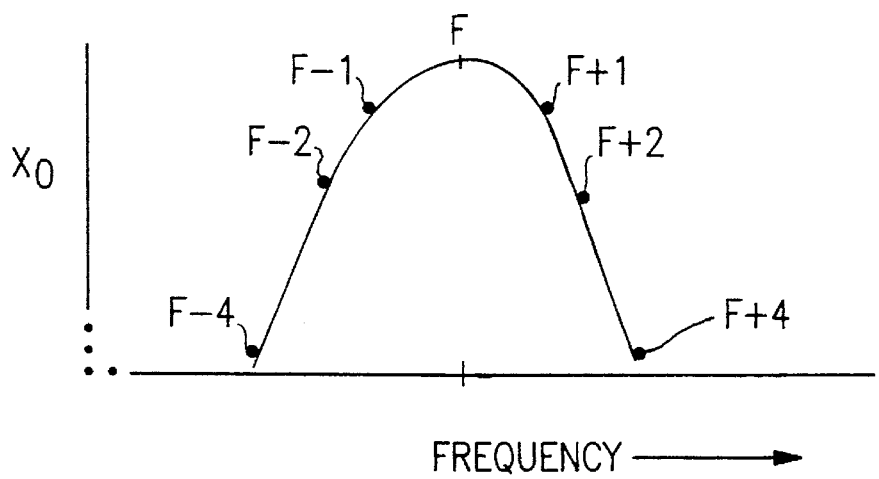

The measurement steps for finding the resonance frequency F, quality factor Q, and equivalent mass m' for a given sample can be carried out as follows:

First the frequency generator is swept between about 600 Hz and 1500 Hz to locate the resonance peak F approximately. Then a careful measurement is made in the neighborhood of the plak to derive the location of the resonance peak F within about 0.5 Hz. A number of measurements of amplitude $X_o(f)$ and frequency $X_o(f)$ are taken for several frequencies at increments above and below the resonance frequency F, as shown generally in FIG. 7. For example, the output level of the microphone 216 is taken for each of the frequencies F, F+1 Hz, F+2 Hz, F+4 Hz, F−1 Hz, F−2 Hz, and F−4 Hz. The factor Q is computed according to the relation:

$$\sqrt{\left(\frac{X_o(F)}{X_o(f)}\right)^2 - 1} = Q(F-f)\frac{2}{F}$$

The several values of Q taken around the resonance are averaged.

Thereafter, the equivalent mass m' of the sample gas is computed, in this example according to the relation:

$$X_o(F) = \frac{A_o/m'}{4\pi^2 F^2} \cdot Q$$

where $A_o$ is the driving frequency amplitude. Each species of refrigerant will have a distinctive pair of values for F and m'.

In a test run of several samples of pure refrigerant and of air, the following results were computed using the test device and method described hereabove:

| Sample | Resonance F (Hz) | Equivalent mass m' |
|---|---|---|
| R134A | 915 | 9.5 |
| R12 | 850 | 13.0 |
| R22 | 1040 | 5.0 |
| Air | 2000 | 2.0 |

For samples of gas mixtures, e.g. R12/R22 mixture some ambiguity can result if the mixture has the same sound velocity as another species, that is, if the resonance F matches another species resonance. However, this ambiguity can usually be resolved by resorting to other characteristics, such as equivalent means m'. For example, a blend of R12 and R22 can be selected to have acoustic characteristics similar to R134A, but this blend will have a measurally distinct mass m'. For example:

| Sample | F | m' |
|---|---|---|
| R134A | 915 | 9.5 |
| R12/R22 | 915 | 10.3 |

Thus the device here will automatically distinguish one species from another, and will also distinguish a pure sample from a contaminated sample. The measurements are highly repeatable and reliable.

The Helmholtz resonators that can be employed in practicing this invention need not be of the straight, tubular design as shown. For example, the resonator could be a right angle device, such as a tee or elbow. The shape of the resonator can be selected to fit the equipment, or to minimize undesirable resonances.

In addition to the task of identifying samples of refrigerants, the devices of this invention can be configured for a feedback and control role. This can be especially useful where two species of a gas must be identified an the blend of the two species must be accurately maintained. For example, the device can be employed in a surgical environment to control a blend of oxygen and anaesthetic being supplied to a patient.

Also, rather than measuring the temperatures of the resonator, means can be incorporated into the device 10 to control and stabilize the temperature.

An acoustic methodology can measure pressure of the inside of the resonator down to about ⅓ atmosphere. This can be used as a check to ensure that the resonator has been purged between samples.

Rather than the lamps L1–L4, many other types of indicators can be employed to indicate the species and quality of the sample gas being tested.

Calibration of the device can be carried out by using a known, available gas, such as shop air, or a standard known refrigerant or refrigerant mixture.

Also, while not specifically shown here, a switch circuit can be included to reverse the roles of the transducers 16,17 which can increase the reliability of the identification.

While this invention has been described in terms of a preferred embodiment, it is clear that the invention is not limited to that embodiment. Rather, many possible modifications and variation would present themselves to persons skilled in the art without departing from the scope and spirit of this invention, as defined in the appended claims.

What is claimed is:

1. A testing device for determining the species and purity of an unknown gaseous substance, comprising:

a Helmholtz resonator having first and second volumes that have fluid communication therebetween through serially arranged first and second necks, said first and second necks each having a predetermined length and cross-sectional area, said first neck providing fluid communication between said first volume and said second neck, said second neck providing fluid communication between said first neck and said second volume, said resonator including means to receive said substance in vapor phase, means to produce at least a first acoustic resonance of the substance within said chamber, and transducer means coupled to an interior of said chamber for generating acoustic vibrations within said chamber and for sensing the acoustic vibrations within the chamber;

a frequency generator for generating a sweep of frequencies across a continuous frequency band that contains said first resonance, including means for applying said sweep of frequencies to said transducer means;

a sensing circuit coupled to said transducer means and to said frequency generator for determining the amplitude of the acoustic vibrations in said chamber over said frequency band and for providing an output signal;

a computer device responsive to said output signal for determining at least a respective first center frequency for said first resonance; determining a first sharpness factor for said first resonance; and identifying the species of said substance and determining the purity of said substance on the basis of said first resonance and said first sharpness factor, and from stored data concerning predetermined species candidates for said substance; and indicator means coupled to said computer device for indicating the species and purity of the substance within said chamber.

2. The testing device of claim 1 further comprising a regulated inlet valve in advance of said chamber for regulating the pressure of the gaseous substance in said chamber at a predetermined pressure.

3. The testing device of claim 2 wherein said regulated inlet valve maintains said pressure at a predetermined pressure on the order of 2 psi.

4. The testing device of claim 2 wherein said regulated inlet valve includes means to permit evacuating the chamber.

5. The testing device of claim 1 wherein said transducer means includes a first electromechanical transducer in acoustic contact with said first volume and a second electromechanical transducer in acoustic contact with said second volume.

6. The testing device of claim 1 wherein said sweep of frequencies extends substantially from 300 Hz to 3000 Hz.

7. The testing device of claim 1 comprising a housing in which said chamber is reposed, and acoustic isolating mounts for mounting said chamber within said housing and isolating the chamber from external vibrations.

8. The testing device of claim 1 further comprising temperature sensing means thermally coupled to said chamber and providing a temperature output to said computer device.

9. Method of determining the species and purity of an unknown gaseous substance, comprising the steps of:

introducing said substance in vapor phase into a resonant chamber which has means to produce first and second fundamental resonances and which includes associated transducer means therein for generating acoustic vibrations within the chamber;

generating a sweep of frequencies across a continuous frequency band that includes said first and second resonances, and including applying said sweep of frequencies to said transducer means;

sensing the strength of the acoustic vibrations in said chamber over said frequency band, and providing an output signal in response to said strength;

determining, based on said output signal, a first center frequency for said first resonance, and a second center frequency for said second resonance;

determining, based on said output signal, a first sharpness factor for said first resonance, and a second sharpness factor for said second resonance; and comparing data based on said center frequencies and said sharpness factors with known data to identify the species and purity of said substance.

10. Method according to claim 9 further comprising, after said introducing step, the steps of sensing temperature of the gaseous substance within the chamber; and temperature-compensating for variations of said temperature from a standard temperature.

11. Method according to claim 9 further comprising, after said introducing step, the step of isolating said chamber from external environmental noise.

12. Method of determining the species and purity of an unknown gaseous substance, comprising the steps of:

introducing said substance in vapor phase into a resonant chamber which has means to produce at least a first fundamental resonance and which includes associated transducer means therein for generating acoustic vibrations within the chamber, said chamber further having first and second volumes that are joined by first and second necks of respective predetermined lengths and respective predetermined areas;

generating a sweep of frequencies across a continuous frequency band that includes said first resonance, and including applying said sweep of frequencies to said transducer means;

sensing the strength of the acoustic vibrations in said chamber over said frequency band, and providing an output signal in response to said strength;

determining, based on said output signal, a first center frequency for said first resonance;

determining, based on said output signal, a first sharpness factor for said first resonance; and comparing data based on said center frequency and said sharpness factor with known data to identify the species and purity of said substance.

13. Method according to claim 12 further comprising, after said introducing step, the steps of sensing temperature of the gaseous substance within the chamber; and temperature-compensating for variations of said temperature from a standard temperature.

14. Method according to claim 12 further comprising after said introducing step, the step of isolating said chamber from external environmental noise.

15. Method of determining the species and purity of an unknown gaseous substance, comprising the steps of:

introducing said substance in vapor phase into a resonant chamber which has means to produce at least a first fundamental resonance and which includes associated transducer means therein for generating acoustic vibrations within the chamber;

generating a sweep of frequencies across a continuous frequency band that includes said first resonance, and including applying said sweep of frequencies to said transducer means;

sensing the strength of the acoustic vibrations in said chamber over said frequency band, and providing an output signal in response to said strength;

determining, based on said output signal, a first center frequency for said first resonance;

determining, based on said output signal, a first sharpness factor for said first resonance; and computing for said substance an equivalent mass based on the strength of said acoustic vibrations, said first resonance center frequency, and said first sharpness factor; and comparing data based on said center frequency and said sharpness factor with known data to identify the species and purity of said substance.

16. Method according to claim 15 wherein said chamber is a Helmholtz chamber having first and second volumes that are joined by a neck of a predetermined length and a predetermined area.

17. Method according to claim 15 further comprising, after said introducing step, the steps of sensing temperature of the gaseous substance within the chamber; and temperature-compensating for variations of said temperature from a standard temperature.

18. Method according to claim 15 further comprising, after said introducing step, the step of isolating said chamber from external environmental noise.

19. Method of determining the species and purity of an unknown gaseous substance, comprising the steps of:

introducing said substance in vapor phase into a resonant chamber which has means to produce at least a first fundamental resonance and which includes associated transducer means therein for generating acoustic vibrations within the chamber;

regulating pressure of said substance within said chamber to a predetermined pressure on the order of 2 psig so that residual gases are purged from said chamber;

generating a sweep of frequencies across a continuous frequency band that includes said first resonance, and including applying said sweep of frequencies to said transducer means;

sensing the strength of the acoustic vibrations in said chamber over said frequency band, and providing an output signal in response to said strength;

determining, based on said output signal, a first center frequency for said first resonance;

determining, based on said output signal, respective a first sharpness factor for said first resonance; and comparing data based on said center frequency and said sharpness factor with known data to identify the species and purity of said substance.

20. Method according to claim 19 wherein said chamber is a Helmholtz chamber having first and second volumes that are joined by a neck of a predetermined length and a predetermined area.

21. Method according to claim 19 further comprising, after said regulating step, the steps of sensing temperature of the gaseous substance within the chamber; and temperature-compensating for variations of said temperature from a standard temperature.

22. Method according to claim 19 further comprising, after said regulating step, the steps of isolating said chamber from external environmental noise.

* * * * *